United States Patent
Wexler

(10) Patent No.: US 10,426,932 B2
(45) Date of Patent: Oct. 1, 2019

(54) METHOD AND APPARATUS FOR INTRODUCING AN INTRAVENOUS CATHETER

(71) Applicant: Toby Wexler, Lafayette, LA (US)

(72) Inventor: Toby Wexler, Lafayette, LA (US)

( * ) Notice: Subject to any disclaimer, the term of this patent is extended or adjusted under 35 U.S.C. 154(b) by 953 days.

(21) Appl. No.: 14/153,833

(22) Filed: Jan. 13, 2014

(65) Prior Publication Data

US 2015/0119852 A1  Apr. 30, 2015

Related U.S. Application Data

(60) Provisional application No. 61/753,776, filed on Jan. 17, 2013.

(51) Int. Cl.
*A61M 25/06*  (2006.01)

(52) U.S. Cl.
CPC .... *A61M 25/0693* (2013.01); *A61M 25/0606* (2013.01)

(58) Field of Classification Search
CPC .......... A61M 25/0606; A61M 25/06–25/0693; A61M 5/427; A61M 5/3293; A61B 5/1422; A61B 2017/00902
See application file for complete search history.

(56) References Cited

U.S. PATENT DOCUMENTS

| | | |
|---|---|---|
| 2,626,604 A | 1/1953 | Nadeau |
| 3,859,998 A | 1/1975 | Thomas et al. |

(Continued)

FOREIGN PATENT DOCUMENTS

| | | | |
|---|---|---|---|
| GB | 1085609 A  * | 10/1967 | ........ A61M 25/0606 |
| RU | 2299078 C2 | 5/2007 | |

OTHER PUBLICATIONS

Infusio, How to fill a syringe, published Aug. 26,2011, https://www.youtube.com/watch?v=Mg5f_4pJFPw.*

(Continued)

*Primary Examiner* — Bhisma Mehta
*Assistant Examiner* — Laura C Schell
(74) *Attorney, Agent, or Firm* — Garvey, Smith & Nehrbass, Patent Attorneys, L.L.C.; Julia M. FitzPatrick; Gregory C. Smith

(57) ABSTRACT

An improved catheter insertion assembly having a transparent tubular member open at each end; a plunger assembly slidable within the tubular member having a stem portion at a first end; and at least a partially transparent chamber having a needle base and sealing member on a second end of the plunger assembly; an elongated tubular needle embedded within the needle base and extending there from with the needle in fluid communication with the transparent chamber; a catheter assembly, a transparent cannula and a transparent hub attached to the second end with the tubular needle passing longitudinally through the cannula; a fluid passage formed between the needle and the cannula so that when the plunger is retracted a vacuum is established within the fluid passage and blood is visibly drawn through the fluid passage into the transparent cannula and if volume permits, blood then would be visible in the transparent hub, and then if volume permits blood would be visible in the void of the catheter body (barrel) created by pulling the plunger; and wherein the tubular needle is threaded through a lumen of the cannula; and wherein the sealing member provides a sliding seal between the plunger assembly and the transparent tubular member; and wherein, a fluid communication exists through the needle into the flashback chamber of the plunger apparatus and through a porous vent. The distal end of the catheter device described herein has the addition of an external flange and dual plunger paddles which allow (Continued)

dynamic positioning of the fingers and one handed operation. Furthermore these structures are ergonomically associated to maximize finger surface area operation; and wherein the user can change the orientation of the beveled needle.

17 Claims, 5 Drawing Sheets

(56) References Cited

U.S. PATENT DOCUMENTS

| | | | | |
|---|---|---|---|---|
| 4,932,945 A * | 6/1990 | Braginetz | ......... | A61M 25/0631 604/195 |
| 4,966,589 A | 10/1990 | Kaufman | | |
| 5,000,740 A | 3/1991 | Ducharme et al. | | |
| 5,242,414 A | 9/1993 | Fischell et al. | | |
| 5,273,540 A * | 12/1993 | Luther | ............... | A61M 25/0631 604/110 |
| 5,279,572 A | 1/1994 | Hokama | | |
| 5,295,970 A * | 3/1994 | Clinton | ............. | A61M 25/0693 604/168.01 |
| 5,520,657 A * | 5/1996 | Sellers | .................. | A61M 25/06 600/575 |
| 5,531,701 A | 7/1996 | Luther | | |
| 5,575,777 A * | 11/1996 | Cover | ................ | A61M 25/0606 604/110 |
| 5,676,656 A * | 10/1997 | Brimhall | ........... | A61M 25/0606 604/162 |
| 5,865,806 A * | 2/1999 | Howell | ............. | A61M 25/0606 604/158 |
| 6,117,112 A * | 9/2000 | Mahurkar | ............. | A61M 5/322 604/110 |
| 6,156,010 A * | 12/2000 | Kuracina | .......... | A61M 25/0693 600/577 |
| 6,213,978 B1 | 4/2001 | Voyten | | |
| 7,125,396 B2 | 10/2006 | Leinsing et al. | | |
| 8,202,253 B1 | 6/2012 | Wexler | | |
| 2002/0177814 A1 * | 11/2002 | Meng | ................. | A61M 25/0606 604/164.07 |
| 2004/0106903 A1 * | 6/2004 | Shue | .................... | A61B 5/1411 604/168.01 |
| 2005/0131350 A1 * | 6/2005 | Shaw | ................ | A61M 25/0606 604/168.01 |
| 2008/0287876 A1 | 11/2008 | Shue et al. | | |
| 2012/0101440 A1 * | 4/2012 | Kamen | .............. | A61B 17/3415 604/164.08 |
| 2013/0131606 A1 * | 5/2013 | Bertocci | ........... | A61M 5/31515 604/221 |

OTHER PUBLICATIONS

Rijnberk et al. "Medical history and physical examination in companion animals". Springer Science & Business Media. Mar. 31, 1995. p. 296.*

PCT International Search Report and Written Opinion of the International Searching Authority for International Application Serial No. PCT/US2015/011139.

* cited by examiner

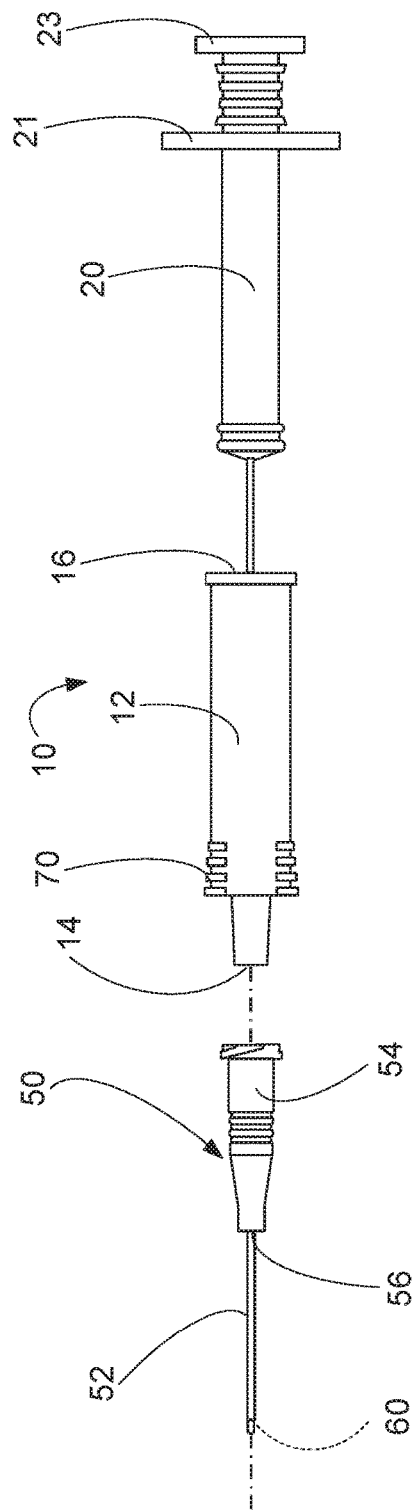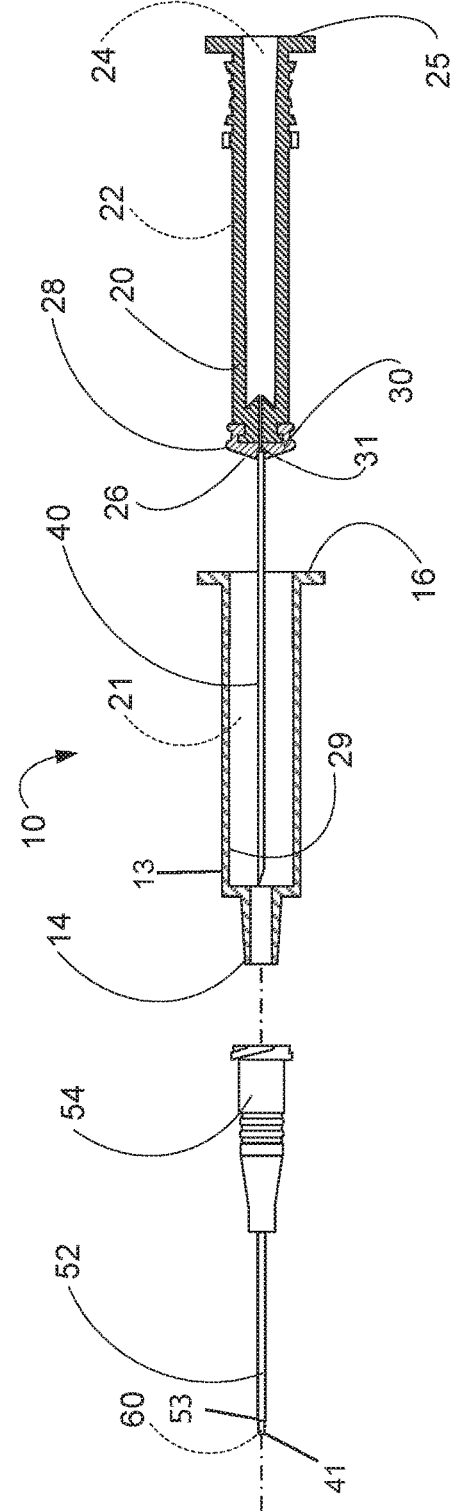

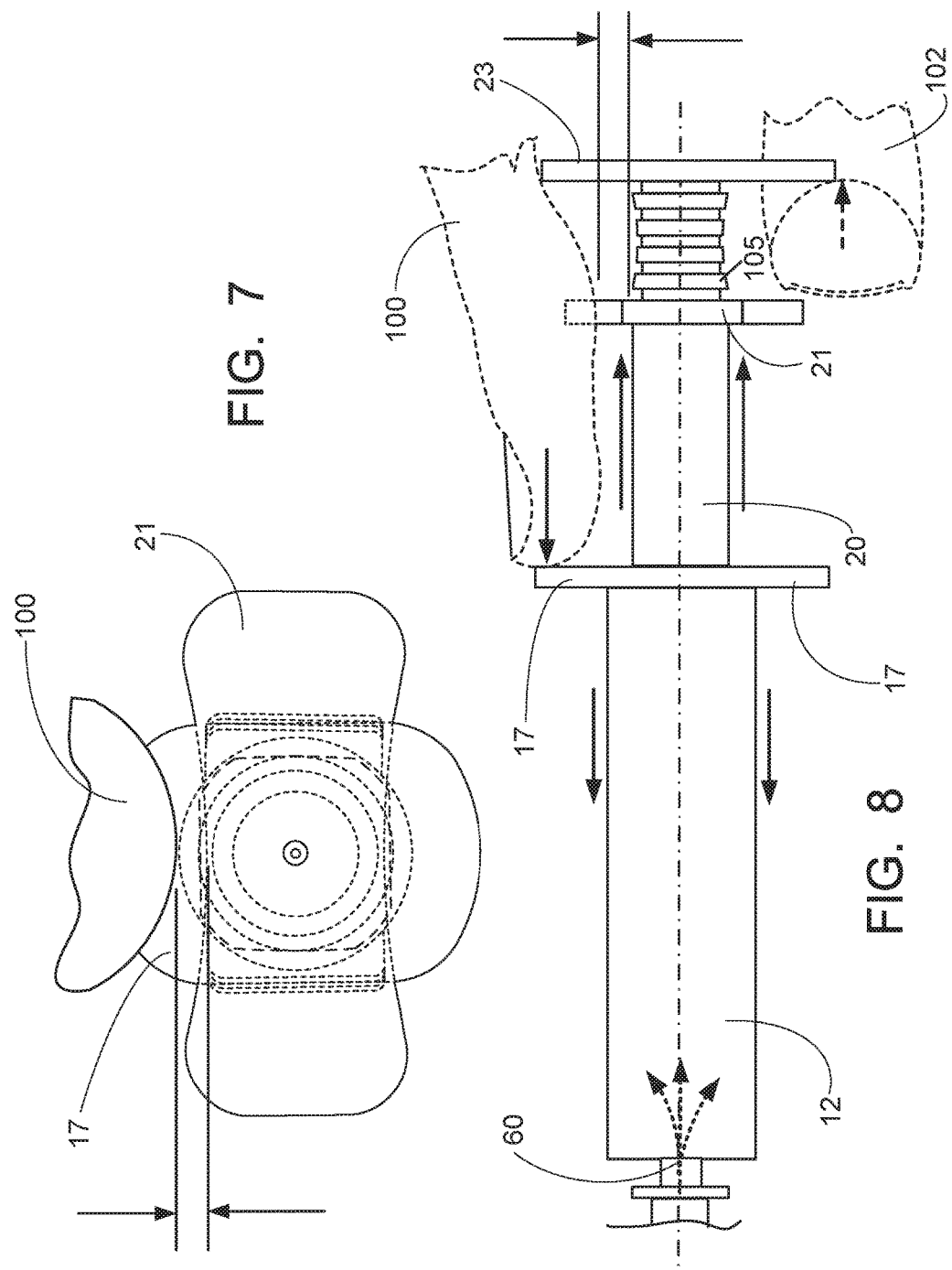

METHOD AND APPARATUS FOR INTRODUCING AN INTRAVENOUS CATHETER

CROSS-REFERENCE TO RELATED APPLICATIONS

This is a nonprovisional patent application of U.S. Provisional Patent Application Ser. No. 61/753,776, filed 17 Jan. 2013, which is hereby incorporated herein by reference. Priority of U.S. Provisional Patent Application Ser. No. 61/753,776, filed 17 Jan. 2013, which is incorporated herein by reference, is hereby claimed.

This application is related to U.S. Pat. No. 8,202,253, which issued on 19 Jun. 2012, entitled "Method and Apparatus for Introducing an Intravenous Catheter", by the same inventor. U.S. Pat. No. 8,202,253, issued on 19 Jun. 2012, is hereby incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates generally to methods and apparatus for introducing a peripheral Intravenous (I.V.) catheter into a subcutaneous blood vessel, and more particularly to an apparatus and method for inserting a cannula into a blood vessel using an insertion apparatus having suction capability for providing a visual indication of the positive placement of the cannula within a blood vessel.

2. General Background

It is a well known, and the established practice for inserting a catheter into subcutaneous blood vessels, to use a cannula and needle assembly for starting an I.V., thereby establishing a continuous medication injection site or venipuncture site to withdraw blood from the blood vessel. Such procedures commonly use an over the cannula needle process whereby a hollow bore needle resides within the cannula hub and which also extends slightly beyond the end of the flexible cannula. The cannula may also be introduced by way of a solid Trocar when there is no need to introduce a medication, or where flashback of arterial blood or fluid is not needed. However, in either case, once the stylet (the needle or Trocar) punctures the blood vessel, the cannula is then deployed forward and off of the end of the needle or Trocar, thereby threading the cannula into the lumen of the vessel. The needle or Trocar is then removed, thereby leaving the cannula threaded within the blood vessel. In either case the needle or Trocar is used to penetrate the subcutaneous layers of the skin and puncture the selected blood vessel and thereby allow insertion of the flexible cannula portion of the catheter assembly to enter the blood vessel. The needle or Trocar must pierce the blood vessel and be at a precise angle of between 20-30 degrees so as to allow the cannula to proceed along the longitudinal bore of the blood vessel. Several factors complicate the successful placement of I.V. catheters. For example, the inherent instability of blood vessels often makes them very difficult to pierce. Furthermore, the needle or Trocar may miss the blood vessel completely, pass through the blood vessel, or the needle or Trocar may enter the blood vessel but the cannula fails to make penetration when the practitioner attempts to deploy the cannula. Frequently, poor cannula placement causes the cannula to be expelled or displaced from the blood vessel by movement of the cannula hub while anchoring the cannula assemble to the patient, or attempting to use the cannula to administer fluid therapy.

A visual indication of needle penetration of the blood vessel is currently achieved by what is known as backflow or flashback of blood into the hub portion of the insertion apparatus. This is a result of blood passing through the needle under arterial pressure into the catheter hub, thus providing a visual indication that penetration of the blood vessel has occurred and that blood is present in the vicinity of the needle. However, this is not an indication that the blood vessel has been penetrated properly or that the cannula tip has fully penetrated the lumen of the blood vessel.

If the practitioner deploys the cannula without proper placement the vein is blown, creating a subcutaneous hematoma around the site. It then becomes very difficult to reacquire the blood vessel because a clot often forms in and around the blood vessel, which prohibits further flashback into the flashback chamber already filled with blood. The practitioner then needs a suction apparatus to withdraw venous blood and possibly reacquire the blood vessel. For this reason it is common for the nurse to place a syringe on the end of the catheter apparatus to provide this suction. This suction helps to relocate the vein because when the needle penetrates a blood vessel, blood can be withdrawn into the syringe. Many inventions are described to reproduce this procedure. Unfortunately, as has been explained, blood withdrawn through the needle only serves to verify that the needle is within the blood vessel. This procedure places the practitioner at the same shortcoming common to all catheters. Locating the vein is only half the problem. Threading the cannula within the lumen of the blood vessel is the current challenge. If the cannula is not well within the lumen of the vessel it will deflect off the vessel wall and blow the vein. Difficulty placing the cannula has also resulted in the use of butterfly catheters which do not use a cannula, but instead leave only a sharp needle within the vessel. Unfortunately, except in very short term use, these will cause trauma to the vein if any movement occurs at the puncture site. Therefore, it would be advantageous to create a suction or negative pressure on the cannula at the most critical location, around the exterior of the needle at the cannula tip, and provide a visual indication of the fact that the cannula is threaded within the blood vessel prior to deploying the cannula and removing the stylet. This would not only facilitate locating the vein, but provide a greater degree of success at actually threading the cannula into the vein once located.

In many cases, using existing technology, the needle derives backflow but has actually passed completely through the selected blood vessel. When the cannula is subsequently deployed, subcutaneous hemorrhage occurs resulting in a large swelling at the site of the venipuncture. Swelling prohibits reacquiring the vein for any further attempts at placing a catheter. This problem frequently occurs when the practitioner is trying to find a vein and actually has the needle in the vein but does not know it due to failure to get a positive flashback in the catheter flash back chamber. The practitioner often attempts to reposition the needle repeatedly searching for the vein. In doing so she actually punctures the vessel, (once or numerous times) with the stylet. Then instead of sliding the catheter cannula off of the needle and into the vein, the practitioner pulls the needle and cannula out of the vein and continues searching. This is a very frequent malfunction of current catheters because of low blood pressure from many common conditions, such as small veins, dehydration, sclerosis of the vein from prior venipuncture, or medical conditions. Under perfect conditions a blown vein does not occur because, when the needle punctures the vein, the positive flashback demonstrates to the practitioner that the cannula should be deployed so as to allow the cannula to seal the hole made by the needle. The needle is then removed and discarded, leaving the cannula in the vein.

Missed attempts to pierce a blood vessel and thereby establish a catheter infusion site result in the need to dispose of the catheter set, composed of a cannula and hub assembly, and a syringe and needle or Trocar, secure the wound site, and seek a new site starting over with a fresh catheter set.

Attempts to improve the procedure by utilizing a cannula visual indicator provides a transparent cannula and a grooved needle to allow the passage of blood along the length of the needle between cannula and the needle. This method relies entirely on capillary action and patient blood pressure. Flow occurs along a grooved needle due to capillary flow and can thus be mistaken as arterial flow through the cannula. In other cases and most often, the needle has passed clear through the vessel, thus producing a false indication of cannula insertion.

As was described in U.S. Pat. No. 8,202,253 (the '253 patent) to the same inventor, Toby Wexler, a need exists to accurately determine the location of cannula tip prior to attempting to thread the catheter cannula into a blood vessel. Although many catheter methods have been described, almost all rely on either capillary action of fluid through a hollow needle or a suction of fluid through a hollow needle. However, since the catheter cannula is shorter than the needle tip, user failure commonly occurs when deploying the cannula because it has failed to penetrate into the lumen of the vessel. Without a suction directly into the cannula and visualization of fluid within the cannula, the user cannot be certain of its location. Although the '253 patent verifies that blood is present in the cannula by visualizing blood in a transparent cannula hub, under cases of low blood pressure or dehydration, there may not be sufficient quantity to reach the hub. Therefore, the need exists to visualize the blood as soon as it begins to fill the cannula.

SUMMARY OF THE INVENTION

The improved catheter apparatus described herein utilizes a transparent cannula which allows the user to visualize the presence of blood before it reaches the transparent hub. Also the need exists to better deploy the plunger as the '253 patent requires two hands to operate. The only mechanism to retract the plunger in the '253 patent is to hold the walls of the tubular member with one hand and pull on the control knob with the other. Because many times the plunger needs to be pulled back and pushed forward numerous times in search of the vessel, the need exists for an improved device which can be operated with one hand so that the user has the other hand free to hold the patients arm or deploy the cannula into the vessel. The catheter device described herein has the addition of an external flange and dual plunger paddles which allow dynamic positioning of the fingers and one handed operation. Furthermore these structures are ergonomically associated to maximize finger surface area operation. The need also exists to be able to change the orientation of the beveled needle, especially in veterinary medicine where many species and many angles of approach are needed, however the '253 patent utilizes a notch which keeps the plunger locked in just one rotational orientation position by use of a chamber attached to a stem. However, the device described herein utilizes a continuous tubular chamber within the plunger which allows the user to rotate the control knob 360 degrees if desired. It is also the intention of the present invention to have bilateral finger gripes which are descending in height on the exterior surfaces of the tubular member to grip the device, as the '253 patent utilizes concave surfaces, and flat surfaces. The '253 patent also uses a chamber attached to the needle in the plunger seat. This chamber acts as a flashback chamber which is standard throughout the art. However blood within the chamber is essentially inaccessible for collection and testing. The present invention utilizes a continuous tubular chamber which allows easy collection of any blood or fluid for laboratory analysis.

Therefore, it is the object of the present invention to provide a cannula insertion apparatus having a better visual means for determining the placement of the cannula.

It is a further object of this present invention to provide finger placement technology which will accommodate a large variety of practioner preferences.

It is a further object of this invention to provide the ability to orient the beveled needle in any rotational position desired and to provide a continuous transparent chamber instead of a chamber and stem.

In an embodiment of the method, a method for inserting a catheter assembly having a cannula and transparent hub comprises the steps of:
  a) providing an apparatus comprising:
    i) a transparent tubular member open at each end with one mammillated end;
    ii) a plunger assembly slidable within said tubular member;
    iii) a transparent chamber having a needle base and sealing member; and
    iv) an elongated tubular needle embedded within said needle base and extending therefrom with said needle in fluid communication with said continuous transparent chamber through an opening in said sealing member;
  b) threading said tubular needle longitudinally through said mammillated end and said hub and cannula;
  c) attaching said hub portion to said mammillated end;
  d) inserting said catheter and tubular needle into a subcutaneous blood vessel thereby allowing pressurized blood to flow into said transparent chamber; and
  e) displacing said plunger thereby defining a void between said sealing member and said mammillated end and thus producing a negative pressure within said void allowing blood to be drawn between said needle and transparent cannula so that a user can identify blood flow within the cannula of the catheter assembly.

In another embodiment of the method, a method for inserting a catheter comprises the steps of:
  a) providing a catheter assembly, comprising:
    i) a transparent tubular member open at each end with one mammillated end;
    ii) a plunger assembly slidable within said tubular member with a knob at one end;
    iii) a transparent chamber into said knob having a needle base and sealing member;

iv) an elongated tubular needle embedded within said needle base and extending there from with said needle in fluid communication with said transparent chamber;

v) a transparent hub member attached externally to said mammillated end having an elongated transparent cannula threaded longitudinally over said tubular needle to a point adjacent said chamber;

b) inserting said catheter and tubular needle into a subcutaneous blood vessel thereby allowing pressurized blood to flow into said transparent chamber; and c) displacing said plunger thereby defining a void between said sealing member and said mammillated end and thus producing a negative pressure within said void allowing blood to be drawn between said needle and cannula and into said transparent hub and void in tubular member so that a user can identify blood flow through either the cannula, hub or void of the improved catheter assembly.

BRIEF DESCRIPTION OF THE DRAWINGS

For a further understanding of the nature and objects of the present invention, reference should be made to the following detailed description taken in conjunction with the accompanying drawings, in which, like parts are given like reference numerals, and wherein:

FIGS. 6A and 6B illustrate an exploded view of the catheter apparatus of the present invention in both side view and cross-section view respectively;

FIG. 7 illustrates the top view of the apparatus of the present invention with a user's thumb placed on the oval flange portion; and FIG. 8 illustrates a side view of the apparatus of the present invention with the thumb of a user's hand placed on the oval flange portion and the index finger of the users hand placed on the underside of the paddle portion to pull the plunger.

DETAILED DESCRIPTION OF THE PREFERRED EMBODIMENT

Figure 1:
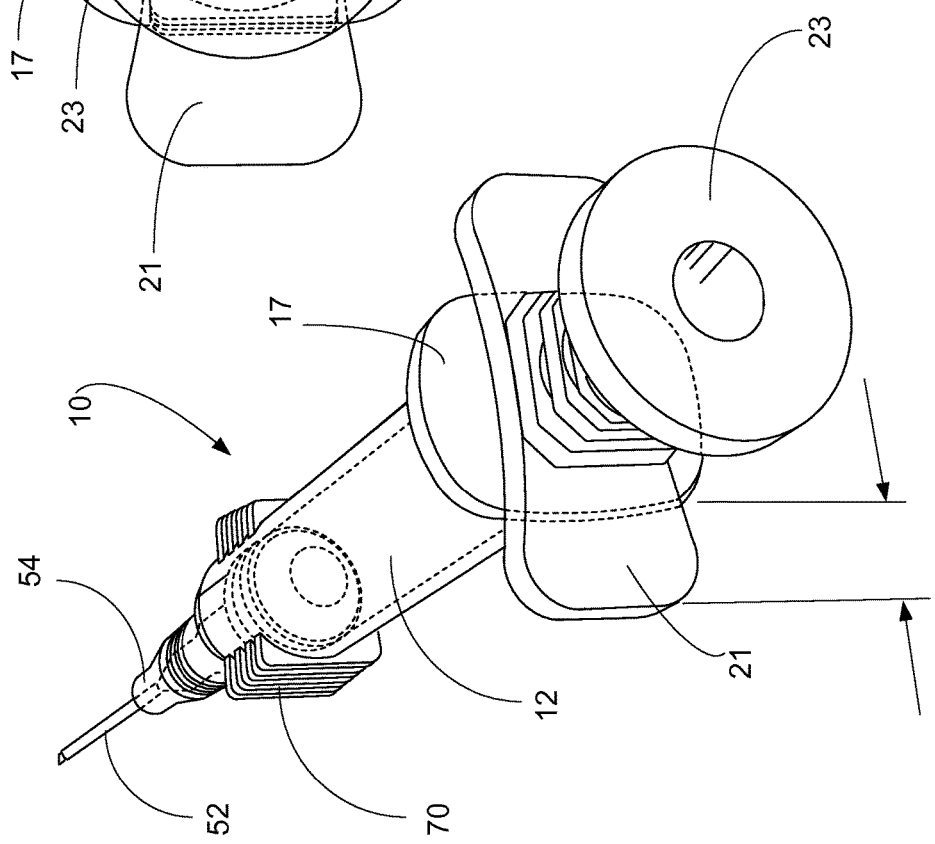
FIG. 1 is an overall view of the improved catheter apparatus of the present invention.
Figure 2:
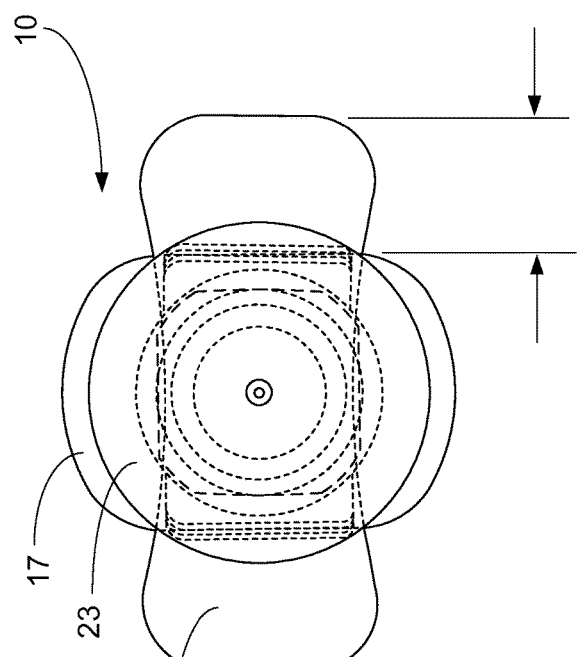
FIG. 2 is a top view of the apparatus of the present invention.
Figure 3:
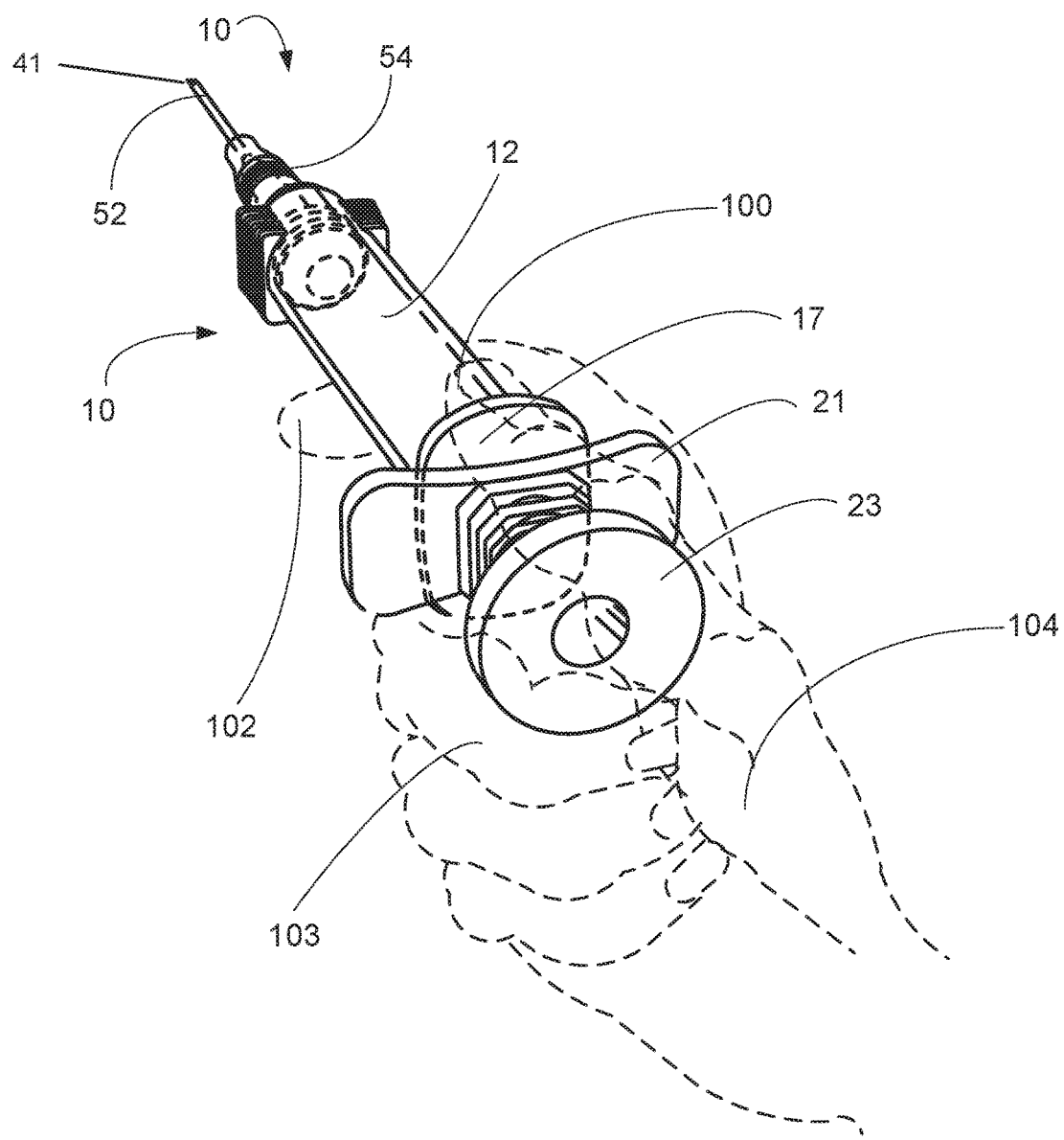
FIG. 3 illustrates the improved apparatus of the present invention as manipulated by a person such as a nurse or medical person.

FIGS. 1-8 illustrate the preferred embodiment of the catheter insertion assembly of the present invention by the numeral 10. As illustrated in the figures, the assembly 10 would include a transparent tubular member 12 open at a first mammillated end 14 and a second end 16. There would be further provided a plunger assembly 20 slidable within chamber 23 within the tubular member 12, with the plunger assembly 20 having a continuous tubular chamber 22 and a vent 24 at the distal end 25 of the member 20. There is further provided, as seen in the drawings, at least a partially transparent chamber needle base 26 and a sealing member 28 on a second end 30 of the plunger assembly 20. As seen in the drawings there is included an elongated tubular needle 40 embedded within a needle base 26 and extending therefrom with the needle 40 in fluid communication with the transparent chamber 22 as seen in FIGS. 6A and 6B. The assembly 10 further includes a catheter assembly 50, having a transparent cannula 52 and a transparent hub 54 attached to the second end 56 of the cannula 52 with the tubular needle 40 passing longitudinally through the cannula 52. Further, there is formed a fluid passage 60 formed between the needle 40 and the cannula 52 so that when the plunger 20 is retracted, a vacuum is established within the fluid passage 60 and blood is drawn through the fluid passage 60 into the transparent hub 54 within the tubular member. In this manner, a user such as a nurse or a medical person, can identify visually blood flow within the cannula 52 and hub 54 of the catheter assembly 10, as seen in the Figures. It should be understood, that the transparent tubular member 12 of the catheter assembly 10 further includes external ridges 70 for gripping the tubular member 12 at a first end and at a distal flange 17 at the second end of the member 12, as seen in FIGS. 1 and 2, for example. Addressing once more the transparent member 12, the plurality of lateral external ridges 70 would preferably be of descending height as seen in FIG. 6A for gripping the tubular member 12 by a user. As is illustrated, there is included an oval flange 17 at the distal end for allowing a user to push the flange 17 with ones thumb 100 without engaging the paddle 21, as seen in FIG. 3. It should be noted that the plunger assembly 20 can be rotated in order to change the rotational orientation of the bevel needle 40 relative to the transparent tubular member 12.

In describing the catheter insertion assembly 10 in another manner, the transparent tubular member 12 opened at each end includes one tapered mammillated first end 14 and one flanged open second end 16. The plunger assembly 20 is slidable within the tubular member 12 and includes a knob end 25 at one end. There is a transparent chamber and fluid communication with the knob end 25 and a needle base 26 and a sealing member 28 at the proximal end.

There is an elongated tubular needle 40 embedded within the needle base 26 and extending therefrom with the needle 40 in fluid communication with the transparent member. As stated earlier, the catheter assembly 10 includes a cannula 52 and a hub 54 attached to the mammillated end 14 with the tubular needle 40 passing longitudinally through the cannula 52. Lastly there is a fluid passage 60 formed between the needle 40 and the cannula 52 for allowing blood flow through the fluid passage 60 into the transparent hub 54. As a vacuum is established within the fluid passage 60, when the plunger 20 is retracted into the tubular member 12, so that a user can verify that the cannula 52 has entered the blood vessel by identifying blood flow first within the transparent cannula 52 and then within the transparent hub 54 of the catheter assembly 10.

Figure 5:
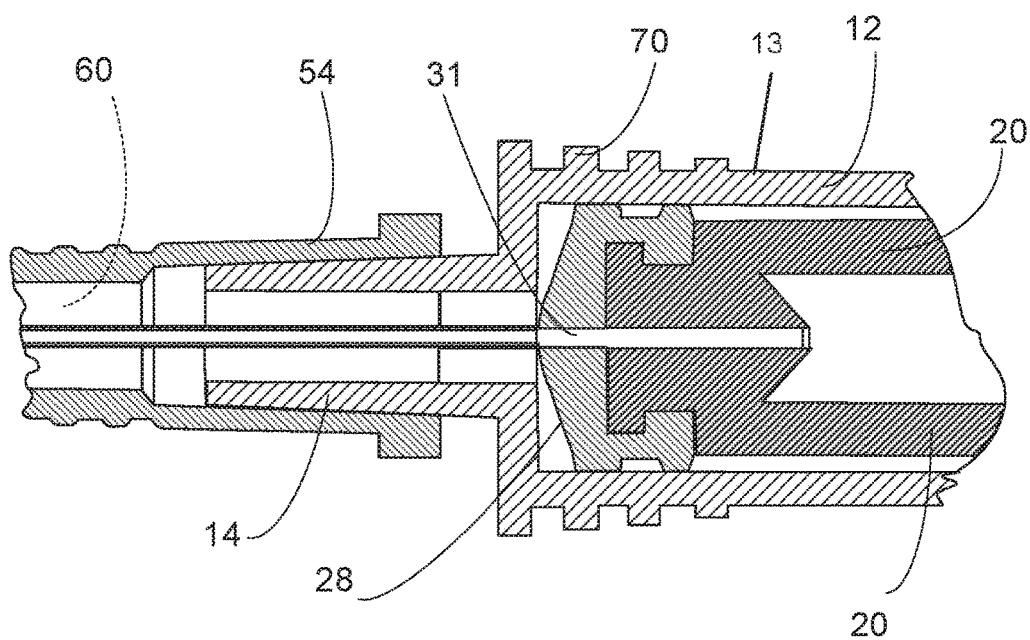
FIG. 5 a partial cross section view of the plunger fully engaged into the syringe body.

Further identifying aspects of the catheter assembly 10 in FIG. 5 as shown, include that the sealing member 28 at the end of the plunger 20 would be in sliding contact with the interior wall 29 of the transparent tubular member 12. Also, the neutral position for the plunger 20 is when the needle base 26 is making contact with the mammilated end 14 as seen in FIG. 5. As further illustrated in FIG. 5, for example, there is provided a central opening 31 in the sealing member 28 which is in coaxial alignment with the opening in the needle 40 secured to the plunger assembly 20, which allows the needle to pass through the opening 31 into the 20 tubular chamber 22 of plunger assembly 20.

Also as shown in FIGS. 3, 5 and 6B the plunger assembly 20 is operable to move within the transparent tubular member 12 between a neutral position and one or more retracted positions. In the neutral position the sealing member 28 and needle base 26 are at or near a junction of the mammillated end 14 of the transparent tubular member 12 and a body 13 of transparent tubular member 12, and wherein the needle 40 passes longitudinally through said transparent cannula 52 and with the needle tip 41 extending exterior to the cannula tip 53. In the one or more retracted positions the needle tip is retracted to an interior of the cannula.

Additionally, the displacement of the plunger 20 from the neutral position can be done by pulling on either the plunger paddle 21 or control knob 23 which retracts the tubular needle 40 into the cannula 52 and defines a void between the seal and the mammillated end 14. The void can be filled with blood or fluid in either way.

Additional features on the new and improved assembly 10 include the feature that the paddle 21 has an hour glass shape which allows a user to make contact with the oval flange 17 without the paddle 21 obstructing the contact. If the paddle were round, contacting the flange 17 could not be accomplished.

Method of the Present Invention

In describing the method of operating the assembly 10, reference is made to FIGS. 7 and 8, where it is noted that both the plunger paddle 21 and control knob 23 are in position with the tubular member flange 17 so as to accommodate the thumb 100 and the forefinger 102 of one hand of a user 104 to operate the plunger 20 within the catheter assembly 10 as illustrated. Finger grips 105 as shown in FIGS. 3-4, 6A and 8, for example, can also be included between plunger paddle 21 and control knob 23.

Figure 4:
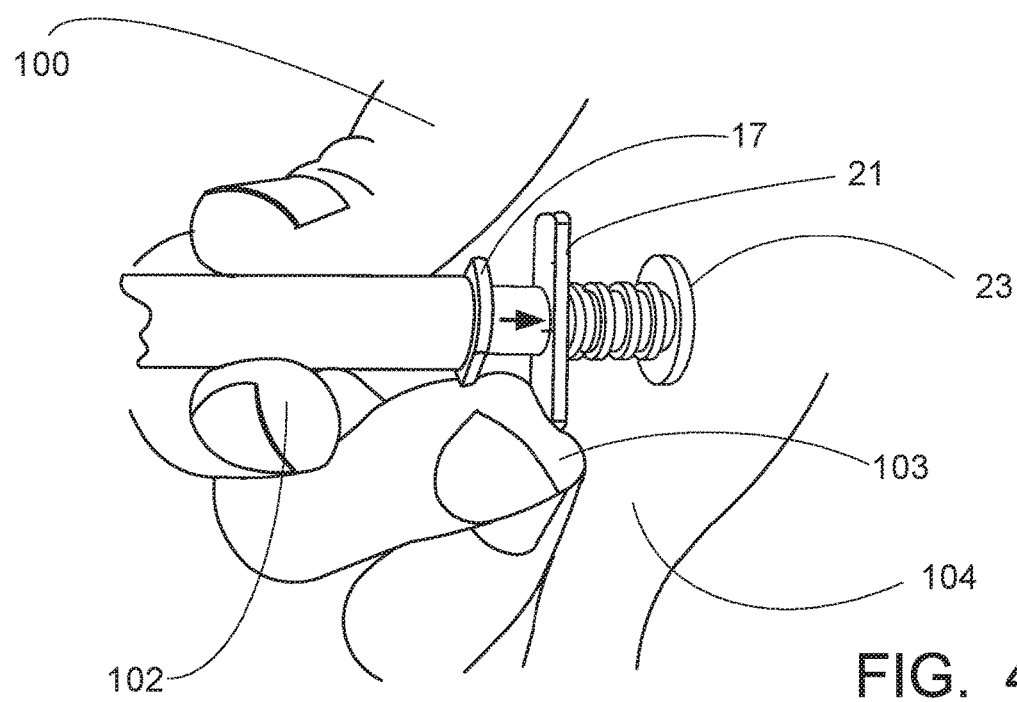
FIG. 4 illustrates an additional position of the catheter in the hands of a user.

Finally, one could describe the method of using the apparatus 10 by two methods of operating the improved catheter assembly 10 utilizing one hand. In one method, as seen in FIG. 4, the index finger 102 and thumb 100 on the exterior wall of tubular member 12 with a third finger 103 on the plunger paddle 21. One would then push the third finger to withdraw the plunger 20. In the alternative, the index finger 102 and thumb 100 could be placed on the external lateral finger gripes 70.

In a second method of operation, as seen in FIG. 3, the thumb dorsal would contact the oval tubular flange 17, the index finger ventral under the tubular member 20, and a third finger 103 ventral on the control knob 23. In operation, one would push with the thumb 100, and pull with the third finger 103 which would withdraw the plunger 20 on the catheter. The method could be described as a method for turning the plunger apparatus 20 so that the rotation orientation of the beveled needle 40 can be changed by rotating the plunger apparatus control knob 23 clockwise or counter clockwise thereby changing rotational orientation of the bevel needle 40 in relation to the tubular member 12.

PARTS LIST 10 catheter insertion assembly
12 transparent tubular member
13 body
14 mammillated
16 second end
17 distal flange
20 plunger
21 plunder paddle
22 tubular chamber
23 knob
24 vent
25 distal end
26 needle base
28 sealing member
29 interior wall
30 second end
31 opening
40 tubular needle
41 needle tip
50 catheter assembly
52 transparent cannula
53 cannula tip
54 transparent hub
56 second end
60 fluid passage
70 external ridges
100 thumb
102 forefinger
103 third finger
104 user
105 finger grip The foregoing embodiments are presented by way of example only; the scope of the present invention is to be limited only by the following claims.

All measurements disclosed herein are at standard temperature and pressure, at sea level on Earth, unless indicated otherwise. All materials used or intended to be used in a human being are biocompatible, unless indicated otherwise.

The invention claimed is:

1. An I.V. catheter insertion assembly comprising:
a) a tubular member that is transparent and has a body, a first end, and a second end, wherein the first end is located at a proximal end of the body and is mammillated, and wherein the second end is located at a distal end of the body;
b) a plunger assembly slidable within the body of said tubular member, the plunger assembly having a chamber that is continuous and transparent, and the plunger assembly having a finger paddle and a control knob at a distal end of the plunger assembly;
c) said chamber of the plunger assembly in fluid communication with said control knob at the distal end of the plunger assembly;
d) a needle base and a sealing member that is air-tight, wherein the sealing member is at a proximal end of the chamber, the sealing member in slidable vacuum sealing contact along an interior surface of the body of the tubular member;
e) a needle that is elongated, beveled, and tubular, the needle embedded within said needle base and extending therefrom with said needle in fluid communication with said chamber, and the needle having a needle tip;
f) an I.V. catheter comprising a cannula, wherein the cannula is flexible, transparent, and is an I.V. cannula, the cannula having a cannula tip and a hub that is transparent, the hub attached to said first end of the tubular member with said needle operable to pass longitudinally through said cannula;
g) the plunger assembly operable to move within the tubular member between a neutral position and one or more retracted positions, wherein in the neutral position the sealing member and needle base are at or near a junction of the first end of the tubular member and the body, and wherein the needle passes longitudinally through said cannula and with the needle tip extending exterior to said cannula tip, and wherein in the one or more retracted positions the needle tip is retracted to an interior of the cannula;
h) a fluid passage formed in a space between said needle and said cannula when the needle passes longitudinally through said cannula; and i) wherein when moving to the one or more retracted positions, retraction of the plunger assembly causes a vacuum in the fluid passage and suction on the cannula tip, said suction visibly drawing blood into the fluid passage and along a longitudinal length of the fluid passage enabling a user to verify that the cannula has entered a blood vessel.

2. The I.V. catheter insertion assembly according to claim 1 wherein displacement of said plunger assembly from said neutral position, can be done by pulling on either the finger paddle of the plunger assembly or the control knob, which retracts said needle to within said cannula.

3. The I.V. catheter insertion assembly according to claim 1 wherein said chamber ends and is open in the control knob.

4. The I.V. catheter insertion assembly in claim 1, wherein after use of the I.V. catheter insertion assembly, the plunger assembly is retractable a sufficient distance within the tubular member to another retracted position wherein the needle tip is shielded by the tubular member to avoid human contact.

5. A method for inserting an I.V. catheter, comprising the steps of:
   a) providing an I.V. catheter assembly, comprising:
      i) a tubular member that is transparent, the tubular member having a body with an end that is open and mammillated;
      ii) a plunger assembly slidable within said tubular member;
      iii) the plunger assembly having a chamber that is transparent, the chamber having a needle base and a sealing member that is air-tight, said sealing member in slidable vacuum sealing contact along an interior wall of the body of the tubular member;
      iv) a needle that is elongated and tubular, wherein the needle is embedded within said needle base and extends therefrom with said needle in fluid communication with said chamber;
      v) an I.V. catheter having a cannula that is an I.V. cannula and which is elongated, flexible, and transparent, the cannula having a cannula tip and a hub member that is transparent, wherein the hub member is attached externally to said end, and wherein the needle is operable to be threaded longitudinally through the cannula;
   b) positioning the I.V. catheter assembly in a neutral position wherein the needle passes longitudinally through the cannula so that a needle tip extends exterior of the cannula tip;
   c) inserting said needle tip and cannula tip of the catheter assembly into a blood vessel thereby allowing blood to flow through the needle and into said chamber for collection or testing; and
   d) verifying that the cannula tip is in the blood vessel by displacing said plunger assembly thereby defining a void between said sealing member and said end and thus producing a negative pressure within said void with suction drawn on the cannula tip, allowing the blood to be drawn along a longitudinal length of a fluid passage in a space between said needle and said cannula and through the end with said hub member attached to said end and into the void in said tubular member so that a user can identify blood flow visible through the cannula, hub member and into the void of the catheter assembly, which blood flow provides a positive indication of proper placement of the cannula tip within the blood vessel.

6. The method in claim 5, wherein following step "d", further comprising a step of retracting the plunger assembly a sufficient distance within the tubular member so that a proximal point of the needle is shielded by the tubular member to avoid human contact after use.

7. An I.V. catheter insertion assembly comprising:
   a) a tubular member that is transparent, the tubular member having a first end, a second end, and a body, wherein the first end is open, is proximal to the tubular member and is mammillated, and wherein the second end is open and distal to the tubular member;
   b) a plunger assembly slidable within said tubular member, the plunger assembly having a chamber that is continuous and transparent;
   c) a needle base and a sealing member that is air-tight, the sealing member coupled to the needle base at a proximal end of the chamber, said sealing member in slidable vacuum sealing contact along a longitudinal interior surface of the body of the tubular member;
   d) a needle that is elongated, beveled, and tubular, the needle having a needle tip and a needle distal end, the needle distal end embedded within said needle base and extending therefrom with said needle in fluid communication with said chamber;
   e) an I.V. catheter comprising a cannula that is an I.V. cannula and which is flexible, and transparent, the cannula having a cannula tip and a hub that is transparent, the hub attached to said first end of the tubular member with said needle operable to pass longitudinally through said cannula;
   f) the plunger assembly operable to move within the tubular member between a neutral position and one or more retracted positions, wherein in the neutral position the sealing member and the needle base are at or near a junction of the first end of the tubular member and the body, and wherein the needle passes longitudinally through said cannula with the needle tip extending to an exterior of the cannula tip, and wherein in the one or more retracted positions, the needle tip is retracted to an interior of the cannula;
   g) a fluid passage formed in a space between said needle and said cannula when the needle passes longitudinally through said cannula; and
   h) wherein retraction of the plunger assembly causes a vacuum in the fluid passage and suction on the cannula tip, said suction visibly drawing blood into the fluid passage and along a longitudinal length of the fluid passage enabling a user to verify that the cannula has entered a blood vessel.

8. The I.V. catheter insertion assembly of claim 7, wherein the chamber is accessible for collection of the blood or a fluid.

9. The I.V. catheter insertion assembly according to claim 7 wherein said tubular member further comprises external ridges for gripping said tubular member at the first end and a flange at the second end.

10. The I.V. catheter insertion assembly according to claim 7 wherein the tubular member comprises lateral external ridges of descending height for gripping the tubular member; and wherein the second end is flanged.

11. The I.V. catheter insertion assembly according to claim 7 wherein said chamber within the plunger assembly is vented to atmosphere through said distal second end.

12. The I.V. catheter insertion assembly according to claim 7 wherein said plunger assembly is operable to be rotated after insertion in the blood vessel, enabling change of a rotational orientation of the needle relative to said tubular member.

13. A method of operating an improved I.V. catheter insertion assembly using one hand, comprising steps of:
   a) providing the I.V. catheter insertion assembly including:
      i) a tubular member having an exterior wall, a first end that is open and proximal to the tubular member and a second end that is open and distal to the tubular member and which includes a flange;
      ii) a plunger assembly slidable within said tubular member, wherein the plunger assembly includes a chamber that is at least partially transparent, and wherein a proximal end of the plunger assembly includes a needle base and a sealing member coupled to the needle base, the sealing member in slidable vacuum sealing contact with a circumference of an inner surface of the tubular member, and wherein a distal end of the plunger assembly includes a plunger paddle spaced apart from a control knob;
      iii) a needle that is elongated and beveled, the needle having a needle tip embedded within said needle base and extending therefrom with said needle in fluid communication with said chamber;
      iv) an I.V. catheter portion comprising a cannula that is flexible and transparent, and a hub that is transparent, the hub attached to the first end of the tubular member, said tubular needle operable to pass longitudinally through the cannula; and
      v) a fluid passage formed between said needle and said cannula when said needle is threaded through said cannula, wherein displacement of the plunger assembly creates a vacuum in the fluid passage and suction on a cannula tip for visibly drawing blood into the fluid passage and along a longitudinal length of the fluid passage;
   b) positioning an index finger and a thumb on the exterior wall of the tubular member of the I.V. catheter insertion assembly, or positioning said index finger on the exterior wall of the tubular member and said thumb on the flange at the second distal end of the tubular member;
   c) positioning a third finger on the plunger paddle;
   d) inserting said needle and said cannula into a blood vessel thereby allowing the mess blood to flow into said transparent chamber;
   e) pushing the plunger paddle in a backward direction with the third finger to cause retraction of the plunger assembly and creation of the vacuum in the fluid passage and the suction on the cannula tip; and
   f) verifying whether the blood is drawn along the longitudinal length of the fluid passage to verify whether the cannula is also in the blood vessel.

14. The method of claim 13 wherein applying pressure to the plunger paddle or control knob with the third finger causes rotation of the plunger assembly within the tubular member in a clockwise or counterclockwise direction to change an orientation of the needle tip.

15. The method of claim 13 wherein the plunger paddle has first and second ends and a middle, wherein the middle is narrower than the first and second ends of the plunger paddle and the first and second ends of the plunger paddle taper downwards towards the middle.

16. The method of claim 15 wherein the plunger paddle has an hourglass shape.

17. The method of claim 15 further comprising collecting the blood and/or a fluid in the chamber for laboratory analysis.

* * * * *